United States Patent
Tyree

[11] 3,999,423
[45] Dec. 28, 1976

[54] ULTRASONIC INSPECTION APPARATUS

[76] Inventor: Bill D. Tyree, 3997 Bellwood Court, Concord, Calif. 94520

[22] Filed: Feb. 2, 1976

[21] Appl. No.: 654,379

[52] U.S. Cl. .......................... 73/67.8 S; 73/71.5 US
[51] Int. Cl.$^2$ ......................................... G01N 29/04
[58] Field of Search ................. 73/67.8 S, 71.5 US; 114/222; 180/1 US

[56] References Cited
UNITED STATES PATENTS

| | | | |
|---|---|---|---|
| 3,682,265 | 8/1972 | Hiraoka et al. | 114/222 X |
| 3,810,515 | 5/1974 | Ingro | 180/1 US |
| 3,844,164 | 10/1974 | Romere | 73/67.8 S |

FOREIGN PATENTS OR APPLICATIONS

| | | | |
|---|---|---|---|
| 978,600 | 12/1964 | United Kingdom | 180/1 US |

*Primary Examiner*—Richard C. Queisser
*Assistant Examiner*—John P. Beauchamp

[57] ABSTRACT

An ultrasonic apparatus for inspecting ferromagnetic surfaces is described. The apparatus comprises a central main frame having two support frames in hinged attachment to it with one support frame on either side of the main frame. Two axles extend through each support frame and each axle has a roller formed at least in part of permanent magnetic material mounted on its outer end and a sprocket wheel mounted on its inner end. Motor drive means are mounted on each support frame. Two sprocket wheels are mounted on the motor drive shaft and a chain drive connects the sprocket wheels on the drive shaft with those on the axles. A support bracket is mounted on the forward end of the main frame. An axle extends through the support bracket and mounted on the axle are a roller and an ultrasonic transducer. The apparatus may be placed on a vertical ferromagnetic wall where it is held by the permanent magnetic material of the rollers. Each pair of rollers is separately driven by the engaged motor so that the apparatus may be caused to move in any direction by varying the rates at which the two pairs of rollers are rotated.

3 Claims, 4 Drawing Figures

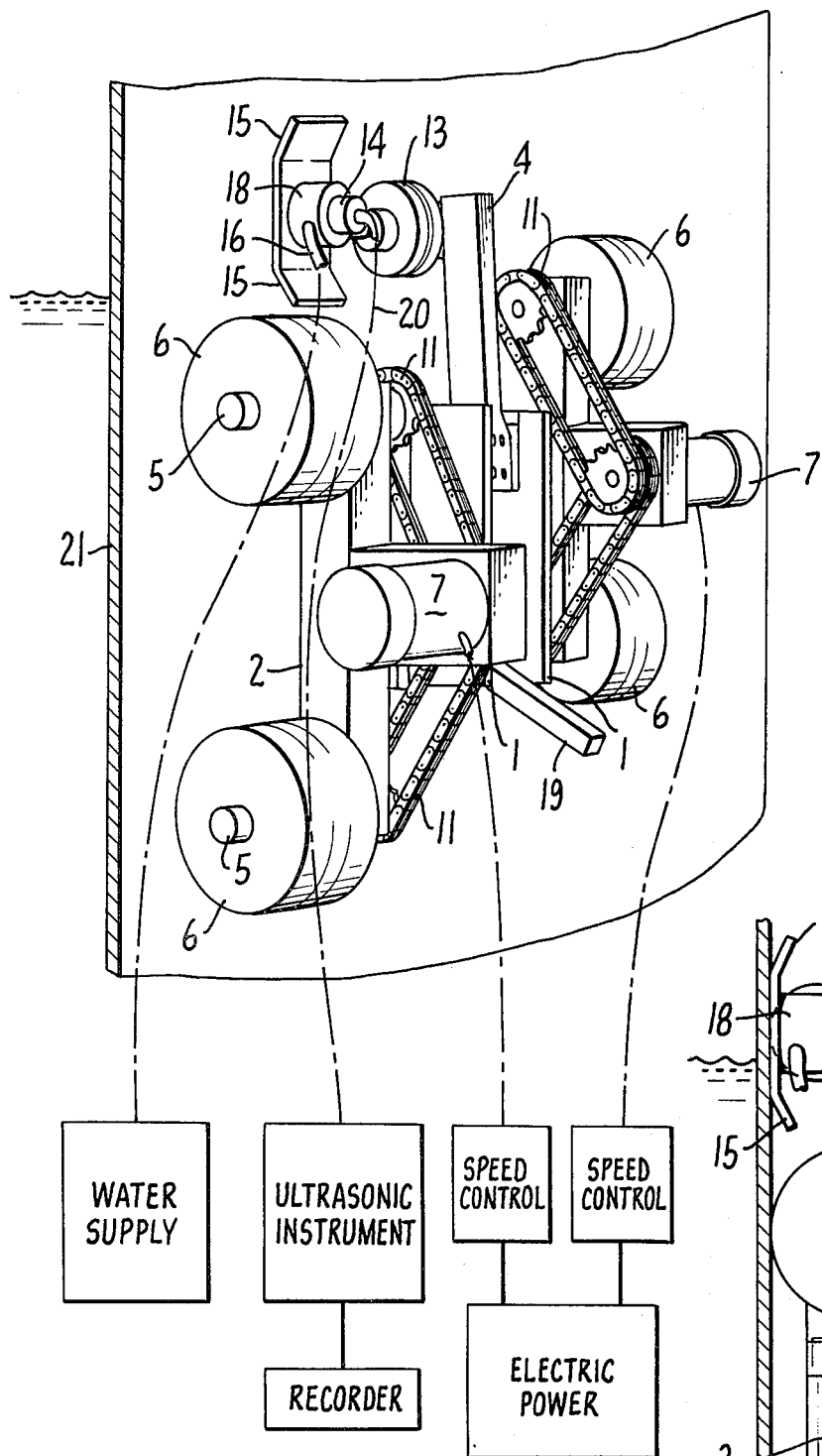
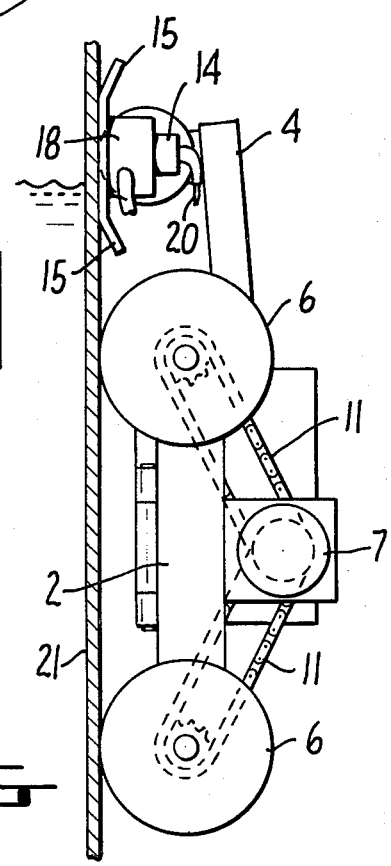
FIG. 1.
FIG. 2.

ULTRASONIC INSPECTION APPARATUS

BACKGROUND OF THE INVENTION

In the past there has been considerable study of the use of ultra sound in non-destructive and inspection of metal. Ultrasonic metal inspection is described in McGraw-Hill *Encyclopedia of Science and Technology* (1971) in volume 8 at page 340. Specific applications of ultra sound to metal inspection are described in U.S. Pats. No. 3,844,164, and 3,850,028.

Ultrasonic inspection apparatus heretofore available has not been well adapted for use in inspection of existing, in use, metal walls which have an extended vertical dimension such as oil refinery tanks, reaction vessels, distillation columns, steel ship hulls, and the like. Oil tanks, for example, are commonly inspected by attaching an ultrasonic transducer mounted on a carriage to a line. An operator positions himself on top of a tank and using a winch pulls in the line, thus raising the ultrasonic transducer from ground level to the top of the tank, hopefully keeping reasonably good contact between the transducer and the tank wall surface as it rises. The ultrasonic transducer is then lowered to the ground, moved laterally and again raised to the top of the tank by the line and this procedure is repeated working around the circumference of the tank.

The present invention provides apparatus capable of making rapid and efficient inspection of vertical ferromagnetic metal walls. The apparatus is placed on the vertical metal surface where it is held to the surface by four rollers formed of permanent magnetic material. The four rollers are arranged in two pairs and each pair is separately driven by a motor. Each pair of rollers may be caused to rotate at a selected rate. The rates for the two pairs may be different with the result that the apparatus can be caused to move in any desired direction, in a curved or straight path and the movement of the apparatus can be directed from ground level adjacent to the metal surface being inspected.

BRIEF DESCRIPTION OF THE INVENTION

The apparatus of the invention is comprised of a central main frame having two support frames in hinged attachment to it with one support frame on either side of the main frame. Two axles extend through each support frame and each axle has a roller formed at least in part of permanent magnetic material mounted on its end furthest from the mounting frame and a sprocket wheel mounted on its inner end. Motor drive means are mounted on each support frame. Two sprocket wheels are mounted on the motor drive shaft and a chain drive connects the sprocket wheels on the drive shaft with those on the axles. The motors have separate power sources and can be driven at different rates. A support bracket is mounted on the forward end of the main frame. An axle extends through the support bracket and mounted on the axle are a roller formed at least in part of permanent magnetic material and an ultrasonic transducer. The apparatus may be placed on a vertical ferromagnetic wall where it is held by the permanent magnetic material of the rollers. Each pair of rollers is separately driven so that the apparatus may be caused to move in any direction by varying the rates at which the two pairs of rollers are rotated.

DETAILED DESCRIPTION OF THE INVENTION

FIG. 1 of the appended drawings shows the apparatus as it would appear when viewed from a point above and to one side of the apparatus.

FIG. 2 is a side view of the apparatus.

Figure 3:
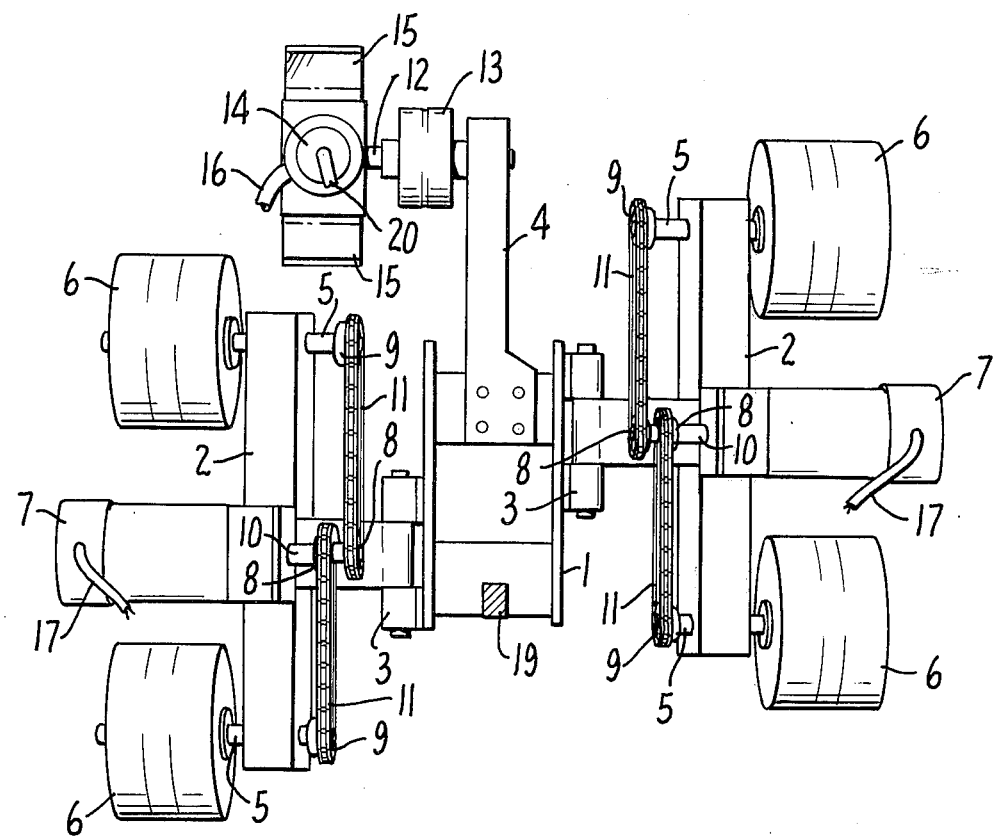
FIG. 3 is a plan view of the apparatus.
Figure 4:
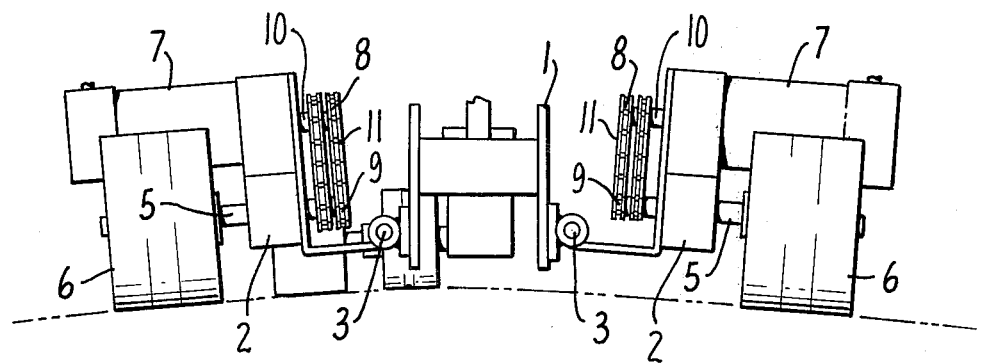
FIG. 4 is an end view of the apparatus.

The apparatus will be described with special reference to FIG. 3 of the drawings. Main frame 1 is a rectangular box-like member to which the other portions of the apparatus are attached as indicated. Mounting frames 2 are shown on either side of the main frame and are attached to the main frame by hinged attachments 3 which permit mounting frames to move vertically up or down relative to the position of the main frame. Bracket 4 extends forward from the main frame and provides support for ultrasonic transducer 14. A pair of axles 5 extend through mounting frames 2, one axle being at either end of each mounting frame. The axles pass through cylindrical holes in the mounting frames and can rotate freely. A roller 6 is mounted on each of the axles 5 outboard of the mounting frame. The rollers are fixed to the axles so that when the axle rotates the roller rotates. A sprocket wheel 9 is mounted on the inboard end of each axle 5. A motor 7 is mounted on the central portion of each mounting frame 2. Motor drive shaft 10 of each motor extends inwardly from the mounting frame and two sprocket wheels 8 are mounted on each of the motor drive shafts. Chain drives 11 engage sprocket wheels 8 and 9 so that when motor drive shaft 10 rotates, axles 5 and rollers 6 are caused to rotate. Axle 12 extends laterally from support bracket 4 and roller 13 and transducer 14 are mounted on axle 12 so that they are free to rotate about the axle. Fenders 15 extend from either side of the transducer assembly and slope upward having the effect of keeping the face of the transducer generally parallel to the surface being inspected. A reservoir 18 surrounds transducer 14 and communicates with waterline 16 which carries water to the area adjacent the emitting face of the transducer where it functions as a coupling agent. Electric cables 17 carry electric current from a power source to motors 7. For convenience, a five wire cable extends from the ground to cable attachment point 19 from which two of the wires pass to each of the motors as indicated in line 17. The fifth wire is a ground wire. Line 20 extends from a power-recorder station on the ground and carries the power required to activate the transducer. In operation of the apparatus, the apparatus is lifted and set on the surface, for instance, of a vertical tank wall so that the four rollers 6 are in contact with the wall surface. The apparatus is held firmly against the tank surface by the permanent magnetic material forming all or part of the rollers. Waterline 16 is attached to a water supply source from which water is pumped through it, electric line 20 extends from the transducer to a power-recorder station and electric lines 17 which carry power to motor 7 are attached to an electric supply source. Each of lines 16, 20 and 17 are long and can be paid out as the apparatus moves over the tanks' surface. To move the apparatus in a straight line along the tanks' surface, the power supplied to both motors is so controlled that the rates of rotation of rollers 6 are the same. In order to turn the apparatus, the pair of rollers on one side of the apparatus is caused to rotate either more rapidly or more slowly than the other pair during the turn. After the turn is completed, all of the rollers can again be rotated at the same rate causing the apparatus to move along a straight line in a new direction. Both pairs of rollers can be rotated in either direction by the drive motors.

The water supply, power supply and recorder apparatus is usually placed in a vehicle which can be taken around the circumference of the tank making it possible for the entire surface of the tank to be inspected without ever moving the apparatus from the tank surface.

Ultrasonic waves are reflected from the interior surface of the metal sheet constituting the tank wall. The reflected waves cause variations in the current movement in line 20 which are detected by the recorder. Corroded areas of the tank wall surface are thinner than the uncorroded areas and the ultrasonic waves are reflected more quickly from these areas and this response variation is noted at the recorder in conventional manner.

As shown in FIG. 1 of the drawings, one of the mounting frames 2 is set farther forward on the main frame 1 than the other. This arrangement puts the two pairs of rollers 6 in a staggered relationship, one pair being set farther forward on the apparatus than the other. This staggered relationship is of great importance when the surface being subjected to inspection is a rough surface having rivet heads or weld seams which extend appreciably above the general surface. The staggered relationship pretty much insures that at least three of the rollers will be in contact with the wall surface even during the passage of the apparatus over rough surface areas. This three point contact is important in order to keep the apparatus generally parallel to the wall surface. Disengagement of two of the rollers will result either in a fall or as a minimum, a disengagement of the emitting surface of the transducer from the tank wall.

A prototype apparatus was built and tested. The weight of the apparatus was approximately 50 pounds, had a total width of about 18 inches and the rollers were each 3½ inches in width and 4⅜ inches in diameter. This apparatus was used to inspect several oil tanks in a refinery tank farm. Because of the possibility of hydrocarbon vapors being encountered in appreciable amounts, both motors were covered with a housing having an inlet and an outlet opening. An air line was extended from the ground to each housing inlet and air was passed into and out of the housing continuously during the inspection of the oil tanks. The inspection of an oil tank 90 feet in diameter and 45 feet high was completed during a single 8 hour shift. The apparatus was run around the tank circumferentially over each course of plates and was then run vertically up and down the tank over each course of plates so that each plate was traversed horizontally and vertically during the inspection.

The strength of the permanent magnetic material in rollers 6 is sufficient to hold the entire apparatus firmly to a vertical ferromagnetic wall and the strength of the permanent magnetic material of roller 13 is sufficient to hold that roller and transducer 14 also mounted on axle 12 in close contact with a vertical ferromagnetic wall.

What is claimed is:

1. A vehicle for inspecting ferromagnetic walls which comprises:
   a. a central main frame,
   b. two mounting frames in hinged attachment to opposite sides of the main frame to permit vertical movement of the mounting frames relative to the longitudinal axis of the main frame,
   c. a forward axle and a rearward axle extending through each mounting frame,
   d. a roller formed, at least in part, of permanent magnetic material fixed on the outer end of each axle,
   e. a drive motor mounted on each mounting frame in driving connection with both axles extending through the mounting frame,
   f. a support bracket attached to the main frame and extending forward from it,
   g. a support axle extending laterally from the support bracket, and
   h. a magnetic roller and an ultrasonic transducer rotatably mounted on said support axle.

2. A vehicle as defined in claim 1 wherein the rollers on one side of the main frame are set farther forward than the rollers on the other side of the main frame.

3. A vehicle for use in carrying out ultrasonic inspection of ferromagnetic metal surfaces which comprises:
   a. a central main frame member,
   b. two mounting frames in hinged attachment to opposite sides of the main frame to permit rotation of the mounting frames relative to the longitudinal axis of the main frame,
   c. a forward axle and a rearward axle extending through each mounting frame,
   d. a wheel-like roller having a permanent magnetic material forming at least a part of its periphery mounted on the outer end of each axle and so attached that rotation of the axle causes rotation of the roller,
   e. a drive motor mounted on each mounting frame,
   f. drive means connecting the axles of each mounting frame with the motor mounted on each mounting frame,
   g. a support bracket attached to the main frame and extending forward from it,
   h. a support axle extending laterally from the support bracket and parallel to the axles extending through the mounting frame,
   i. a magnetic roller rotatably mounted on said support axle, and
   j. an ultrasonic transducer mounted on said support axle.

* * * * *